United States Patent
Roundhill

(10) Patent No.: US 6,951,543 B2
(45) Date of Patent: Oct. 4, 2005

(54) AUTOMATIC SETUP SYSTEM AND METHOD FOR ULTRASOUND IMAGING SYSTEMS

(75) Inventor: David N. Roundhill, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/825,932

(22) Filed: Apr. 16, 2004

(65) Prior Publication Data

US 2004/0267124 A1    Dec. 30, 2004

Related U.S. Application Data

(60) Provisional application No. 60/482,545, filed on Jun. 24, 2003.

(51) Int. Cl.[7] .............................................. A61B 8/00
(52) U.S. Cl. .................................................... 600/443
(58) Field of Search ................................ 600/437, 443, 600/447, 453–456; 128/916; 73/625–626

(56) References Cited

U.S. PATENT DOCUMENTS

| | | | |
|---|---|---|---|
| 4,271,842 A * | 6/1981 | Specht et al. ............... | 600/443 |
| 5,215,094 A | 6/1993 | Franklin et al. | |
| 5,293,326 A * | 3/1994 | Arima et al. ................. | 702/39 |
| RE35,148 E | 1/1996 | Lizzi et al. | |
| 5,697,372 A | 12/1997 | Hughes | |
| 5,795,297 A * | 8/1998 | Daigle ........................ | 600/447 |
| 6,101,407 A * | 8/2000 | Groezinger ................. | 600/407 |
| 6,126,598 A | 10/2000 | Entrekin et al. | |
| 6,349,143 B1 * | 2/2002 | Hastings et al. ............ | 382/128 |
| 6,370,413 B1 * | 4/2002 | Alvarez et al. ............. | 600/407 |
| 6,447,453 B1 * | 9/2002 | Roundhill et al. .......... | 600/443 |
| 6,464,636 B1 * | 10/2002 | Kinicki et al. ............. | 600/437 |
| 6,520,912 B1 * | 2/2003 | Brooks et al. ............. | 600/437 |

* cited by examiner

Primary Examiner—Francis J. Jaworski
(74) Attorney, Agent, or Firm—W. Brinton Yorks, Jr.

(57) ABSTRACT

A diagnostic ultrasound imaging system displays a gallery of ultrasound images each of which was obtained using a different setting for the imaging system. One of the images in the gallery is selected, and the imaging system is then set up to use the setting that was used to obtain the selected ultrasound image. The images displayed in the gallery may be obtained using different settings or different combinations of settings, and settings may be selected by selecting one or more images from each of several sequentially displayed galleries.

22 Claims, 5 Drawing Sheets

AUTOMATIC SETUP SYSTEM AND METHOD FOR ULTRASOUND IMAGING SYSTEMS

This invention claims the benefit of Provisional U.S. Patent Application Ser. No. 60/482,545, filed Jun. 24, 2003.

The invention relates diagnostic ultrasound imaging systems, and, more particularly, to a diagnostic ultrasound imaging system that automatically sets up the acquisition and/or display parameters and operating modes for the imaging system to optimally display an ultrasound image.

The quality of an image obtained using a diagnostic ultrasound imaging system is a function of numerous acquisition and/or display parameters and/or selected operating modes. These parameters are generally adjusted and operating modes selected by a sonographer or other healthcare professional prior to and during an ultrasound examination to optimize an image displayed by the system for the desired diagnosis. Acquisition parameters include transmit parameters like transmit frequency, transmit power, transmit beam location and transmit depth as well as receive parameters like the number of scan lines processed, the number of scan lines interpolated between transmit lines, and aberration correction values. Display parameters include, for example, the dynamic range, resolution, contrast and persistence of a displayed image. Operating modes that may be selected during an ultrasound examination include, for example, spatial compounding, harmonic imaging, 2-dimensional or 3-dimensional imaging and Doppler imaging. All of these display and acquisition parameters and operating modes as well as other similar parameters and operating modes will sometimes collectively be referred to as the "settings" of an ultrasound imaging system.

As can be appreciated, the large number of possible settings results in a vast number of possible setting combinations. As a result, it can be very difficult and time consuming to set up an ultrasound imaging system with the optimum settings. To lessen the burden of manually making these settings, techniques have been developed to automatically select various combinations of settings. For example, some conventional ultrasound imaging systems include means to select combinations of settings based on the type of examination being performed. A first combination of settings theoretically optimized for conducting an obstetrics ultrasound exam may be selected by actuating a button labeled "OB," a second combination of settings theoretically optimized for conducting a cardiac ultrasound exam may be selected by actuating a button labeled "CARDIAC," a third combination of settings theoretically optimized for conducting a gastro-intestinal ultrasound exam may be selected by actuating a button labeled "GI," etc. Although this capability can reduce set up times and provide better ultrasound images, they nevertheless may fail to optimize the settings for the specific ultrasound examination being conducted. For example, the "CARDIAC" settings may be optimized to conduct a cardiology exam on a patient having an average body habitus, but the patient actually being examined may be heavier, more muscular, or in other respects different from than the average patient. In such a case, the settings automatically selected by pressing the "CARDIAC" button may not be optimized for the specific patient being examined. In such cases the conventional approach taken by the sonographer is to vary the settings of one or more parameters and observe the effect if any of the new settings on the ultrasound image.

Ultrasound imaging systems have also included means for allowing the settings used for an ultrasound exam to be stored for future use. Although imaging systems having this preset storage capability can be easily and quickly set up for patients for which the systems previously have been optimized, it may still be necessary to adjust the settings of imaging parameters and observe their effect on the image whenever a new patient is being diagnosed.

A need therefore exists for an ultrasound imaging system that can be easily and quickly set up in an optimum manner for a specific patent who is to be examined using the system.

An ultrasound imaging system and method of setting-up an ultrasound imaging system using galleries of ultrasound images displayed by the system. Each of the images shown in each gallery is obtained using a different setting or group of settings, e.g., acquisition or display parameter or operating mode, for the ultrasound imaging system. By viewing the gallery the user can see the effects of different settings on an ultrasound image of the patient currently being examined. By selecting at least one of the ultrasound images displayed in each gallery, the setting or settings used to obtain the selected image are automatically selected. The ultrasound imaging system is then set up using the setting or settings for the selected ultrasound image or images. The imaging system display may simultaneously display a large number of images obtained with different settings, and more than one image may be selected to select multiple settings. The images shown in one or more galleries may also be obtained using different combinations of settings so that selecting one of the images automatically selects that combination of settings. The combination of settings used to obtain the displayed images may be based on the type of ultrasound exam that is to be conducted.

Figure 1:
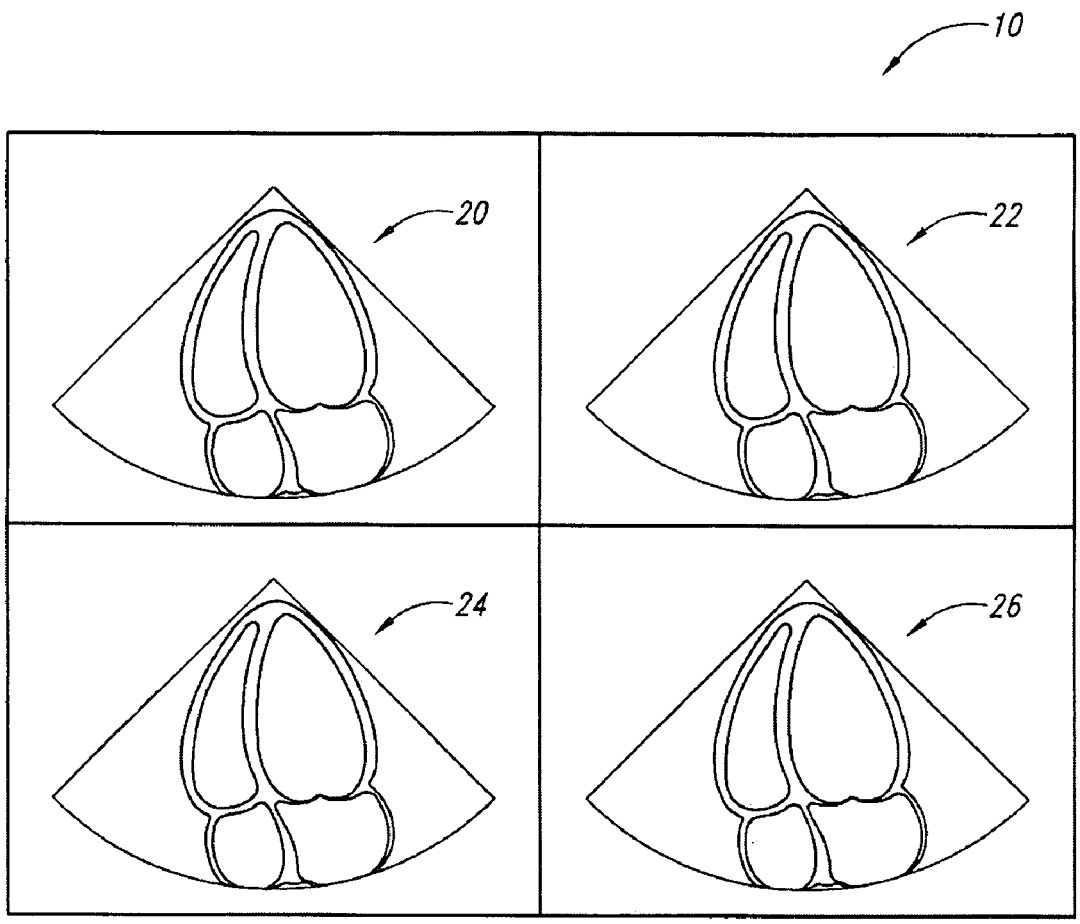
FIG. 1 is a screen shot of a display used in an ultrasound imaging system according to one embodiment of the invention to select one of four acquisition or display parameters.

FIG. 1 shows a viewing screen 10 of a display used in an ultrasound imaging system (not shown) according to one embodiment of the invention. The screen 10 shows a gallery of four images 20, 22, 24, 26 obtained from a patient being examined using the imaging system. Each of the images 20–26 is obtained using a different display or acquisition parameter or different operating mode. For example, the image 20 is obtained by spatial compounding, the image 22 is obtained using a large dynamic range setting, the image 24 is obtained using a low velocity wall filter setting, and the image 26 is obtained using a moderate image persistence setting. The persistence may be adjusted, for example, as disclosed in U.S. Pat. No. 5,215,094, which is incorporated herein by reference. The sonographer or other operator of the system selects the image that provides the best presentation of the features of interest by suitable means, such as by "clicking" on the selected image with a pointing device. The system then automatically uses the parameter setting of the selected image for a subsequent ultrasound examination.

The images 20–26 shown in the gallery of FIG. 1 can be static images, or selected ones can be loops of images which depict the effects of parameters under dynamic imaging conditions.

After an image having the optimum persistence setting is selected, the screen 10 may display another gallery of images (not shown) in which another display or acquisition parameter or group of parameters, such as transmit frequency, is varied. The system operator again selects the image that provides the best presentation of the features of interest, and the system automatically uses that transmit frequency or parameter in combination with the previously selected parameter settings for an ultrasound examination. In like manner, the screen 10 subsequently displays galleries of images in which display or acquisition parameters are varied, the optimum images are selected, and the settings producing such images are used in combination with the previously selected settings. After the imaging system has been set up by selecting images from one or more galleries, the settings may be manually adjusted in an effort to further optimize the performance of the system if desired.

Figure 2:
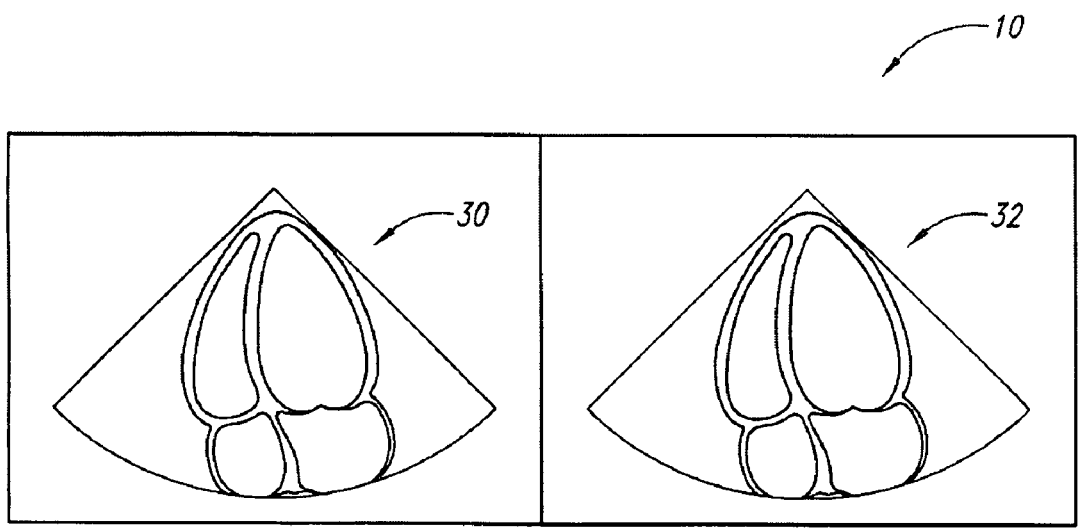
FIG. 2 is a screen shot of a display used in an ultrasound imaging system according to one embodiment of the invention to select one of two operating modes.

With reference to FIG. 2, the viewing screen 10 may also show a gallery consisting of two images 30, 32, one of which 30 was obtained using a first operating mode and the other of which 32 was obtained using a second operating mode. For example, the image 30 was obtained using spatial compounding, and the image 32 was obtained without spatial compounding. By selecting the image 30, spatially compounding is automatically selected for use in an examination along with the previously selected settings. In like manner, the screen 10 may display images using other operating modes so that selecting the view that best displays an image automatically selects that operating mode.

Figure 3:
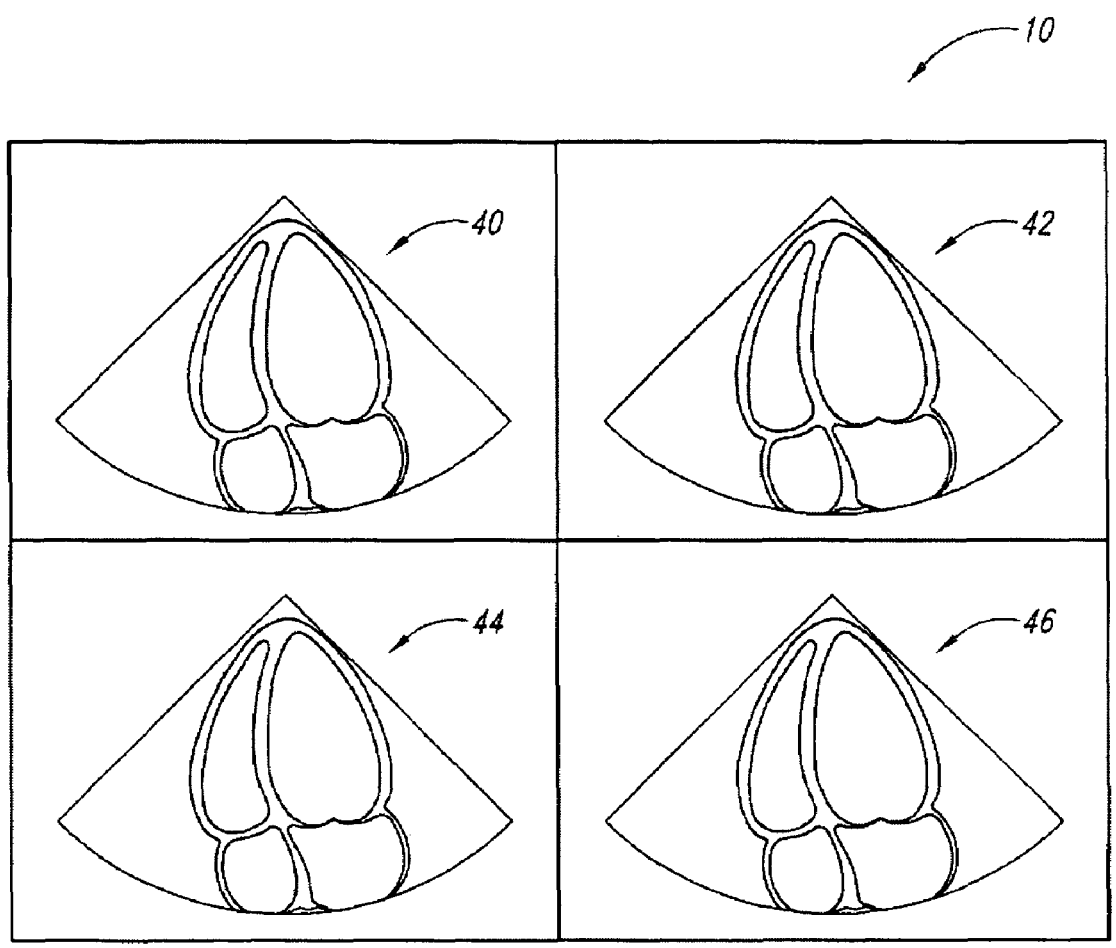
FIG. 3 is a screen shot of a display used in an ultrasound imaging system according to still another embodiment of the invention to select one of four combinations of settings.

In another embodiment of the invention shown in FIG. 3, the screen 10 shows gallery of images 40–46 each of which is obtained using a different predefined combination of settings. The combination of settings may be applied to the ultrasound system as a macro instruction set, for example. By selecting the image that best displays a feature of interest, the system operator automatically selects the combination of settings that produced that image. The images 40–46 may also be selected iteratively in which the image selected in each gallery is displayed in a subsequent gallery along with images obtained using a new combination of settings. The images 40–46 initially displayed in the embodiment of FIG. 3 may also be selected based on the type of ultrasound examination that is to be conducted. For example, images obtained using a first group of setting combinations would be initially displayed for an obstetrics exam, images obtained using a second group of setting combinations would be initially displayed for a cardiac exam etc. Once an image was selected from the initial images, the combination of settings used to create that image can be used either for an ultrasound exam or in a subsequent gallery of images. Again, the settings may also be manually adjusted if desired.

Among the parameters that may be varied in the gallery of images are line density, focal zones, dynamic range, transmit and receive frequencies, resolution, penetration, transmit power, sector width, grayscale mapping, and number of multilines. Flow or motion parameters which may be varied include wall filter settings, color map, frame rate, velocity range, frequency compounding, filter settings, and steering angle. Imaging modes which may be shown in the gallery include grayscale mode, Doppler modes such as colorflow, power Doppler and tissue Doppler imaging, spatial compounding, harmonic mode, and fundamental mode. The images can be shown in two or three dimensions, graphically (e.g., spectral Doppler), statically or dynamically.

Figure 4:
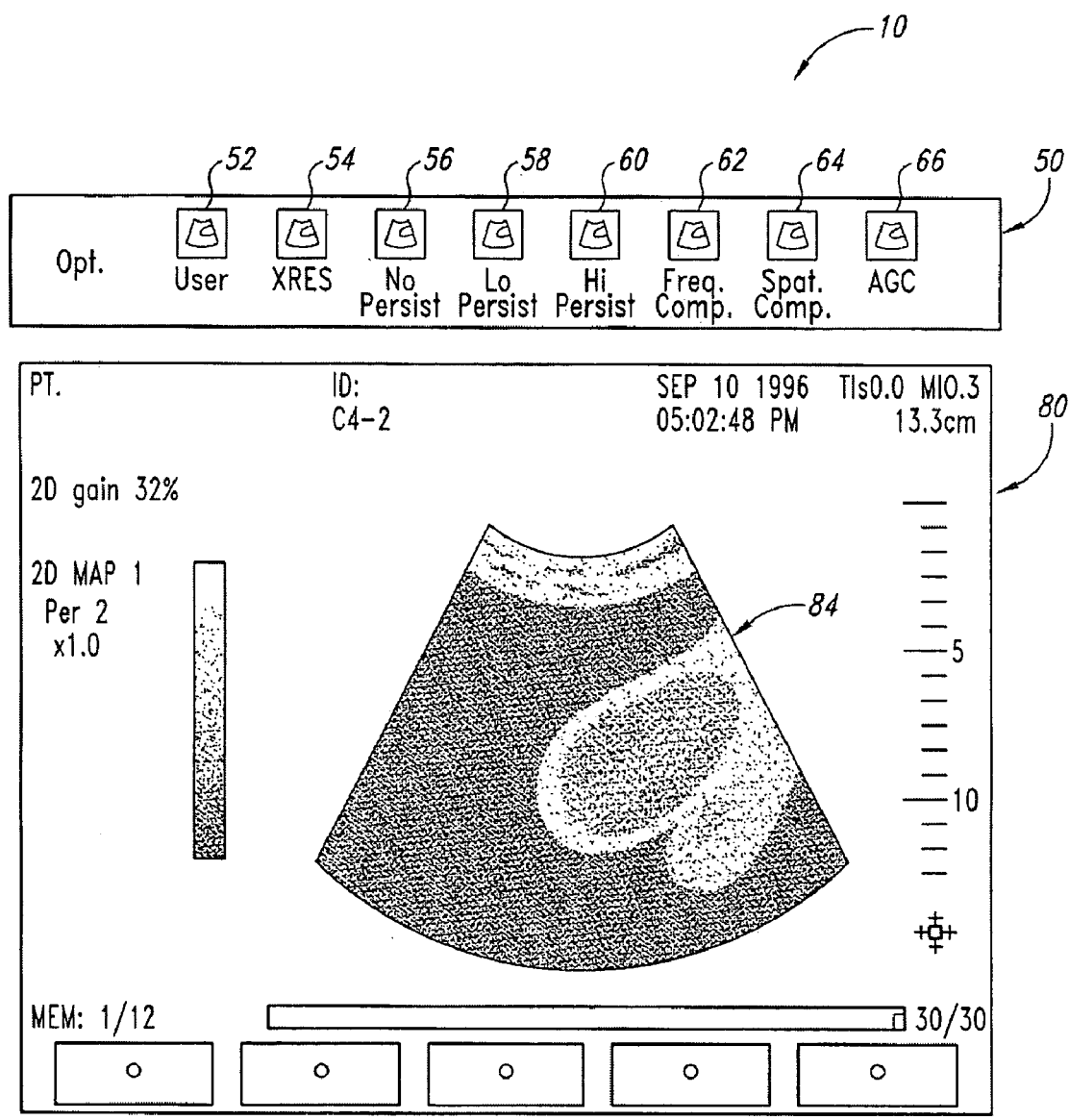
FIG. 4 is a screen shot of a display used in an ultrasound imaging system according to still another embodiment of the invention in which one or more settings can be selected.

Another embodiment of the invention is shown in FIG. 4. The viewing screen 10 includes a first window 50 showing several thumbnail images 52–66 that are obtained using different settings for the same image data. As shown in FIG. 4, the image 52 is obtained using a normal operating mode, the image 54 is obtained using an image smoothing filter, the images 56–60 are obtained using three different levels of persistence, the image 62 is obtained using frequency compounding, the image 64 is obtained using spatial compounding, and the image 66 is obtained using automatic gain control. By displaying all of the thumbnail images 52–66 adjacent each other in the same window 50, it is readily apparent which settings should be used to optimize the image obtained with the imaging system.

The viewing screen 10 also includes a second window 80 that includes a full size image 84 as well as other data displayed around the periphery of the image 84. The image 84 is obtained using the settings selected by selecting one or more of the thumbnail images 52–66. As a result, the settings to obtain the image 84 can be quickly and easily optimized. Furthermore, as each of the thumbnail images 52–66 is selected, the effect of using the corresponding settings will be readily apparent by viewing the resulting change to the image 84.

Figure 5:
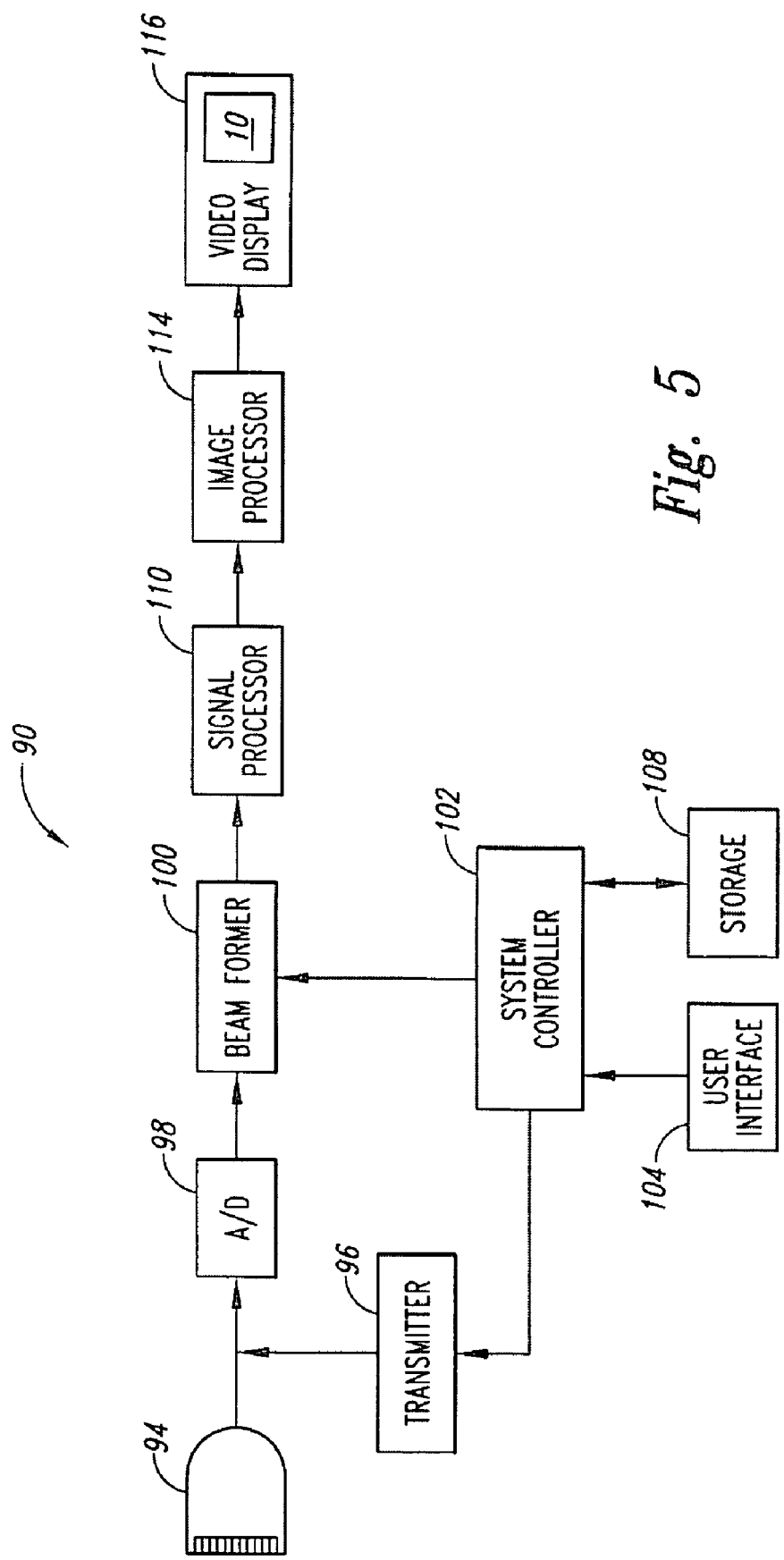
FIG. 5 is a block diagram of an ultrasound imaging system according to one embodiment of the invention.

FIG. 5 shows one embodiment of an ultrasound imaging system 90 that is capable of providing one or more of the viewing modes shown in FIGS. 1–4. The system 90 includes a scanhead 94 that transmits beams of ultrasound at different angles over an image field and receives ultrasound echoes from tissues and fluids beneath the scanhead 94. The transmit beams are generated by a transmitter 96, which controls the phasing and time of actuation of each element of the scanhead 94 so as to transmit each beam from a predetermined origin and at a predetermined angle.

Ultrasound echoes returned from along each scanline are received by the elements of the scanhead 94, digitized as by an analog to digital ("A/D") converter 98, and coupled to a digital beamformer 100. The beamformer 100 delays and sums electrical signals from the scanhead 94 that correspond to the received ultrasound echoes to form a sequence of focused, coherent digital echo samples along each scanline. The transmitter 96 and beamformer 100 are operated under control of a system controller 102. The system controller 102 operates responsive to the settings of controls on a user interface 104 manipulated by the operator of the ultrasound system. As explained above, the user interface 104 includes controls for selecting each of a several images displayed on the screen 10 as well as controls for manually adjusting each of the display and acquisition parameters and manually selecting each of the operating modes. The system controller 102 controls the transmitter 96 to transmit the desired number of scanline groups at the desired angles, transmit energies and frequencies. The system controller 102 also controls the digital beamformer 100 to properly delay and combine the received echo signals for the apertures and image depths used. Finally, the system controller 102 is coupled to a storage device 108 that stores settings selected by the system operator, and optionally stores settings from prior ultrasound examinations. The storage device 108 may be, for example, a disk drive unit. The function performed by the system controller 102 will depend upon the operating capabilities of the imaging system as well as the settings selected by the operator. For example, the system controller 102 may perform Doppler processing or spatial compounding if the system 90 has been provided with those capabilities and one or both of those modes have been selected by the operator.

The scanline echo signals from the digital beamformer 100 are coupled to a signal processor 110 in accordance with the settings of the imaging system 90. For example, the signal processor 110 may perform Doppler processing by conventional means, spatial compounding as disclosed in U.S. Pat. No. 6,126,598, which is incorporated herein by reference, frequency compounding as disclosed in U.S. Pat. No. Re. 35,148, which is incorporated herein by reference, automatic gain control as disclosed in U.S. Pat. No. 5,697,372, which is incorporated herein by reference, harmonic imaging, etc. The signals from the signal processor 110 are coupled to an image processor 114, which performs scan conversion and video processing. Video signals from the image processor 110 are then applied to a video display 116, which includes the viewing screen 10 shown in FIGS. 1–4.

Figure 6:
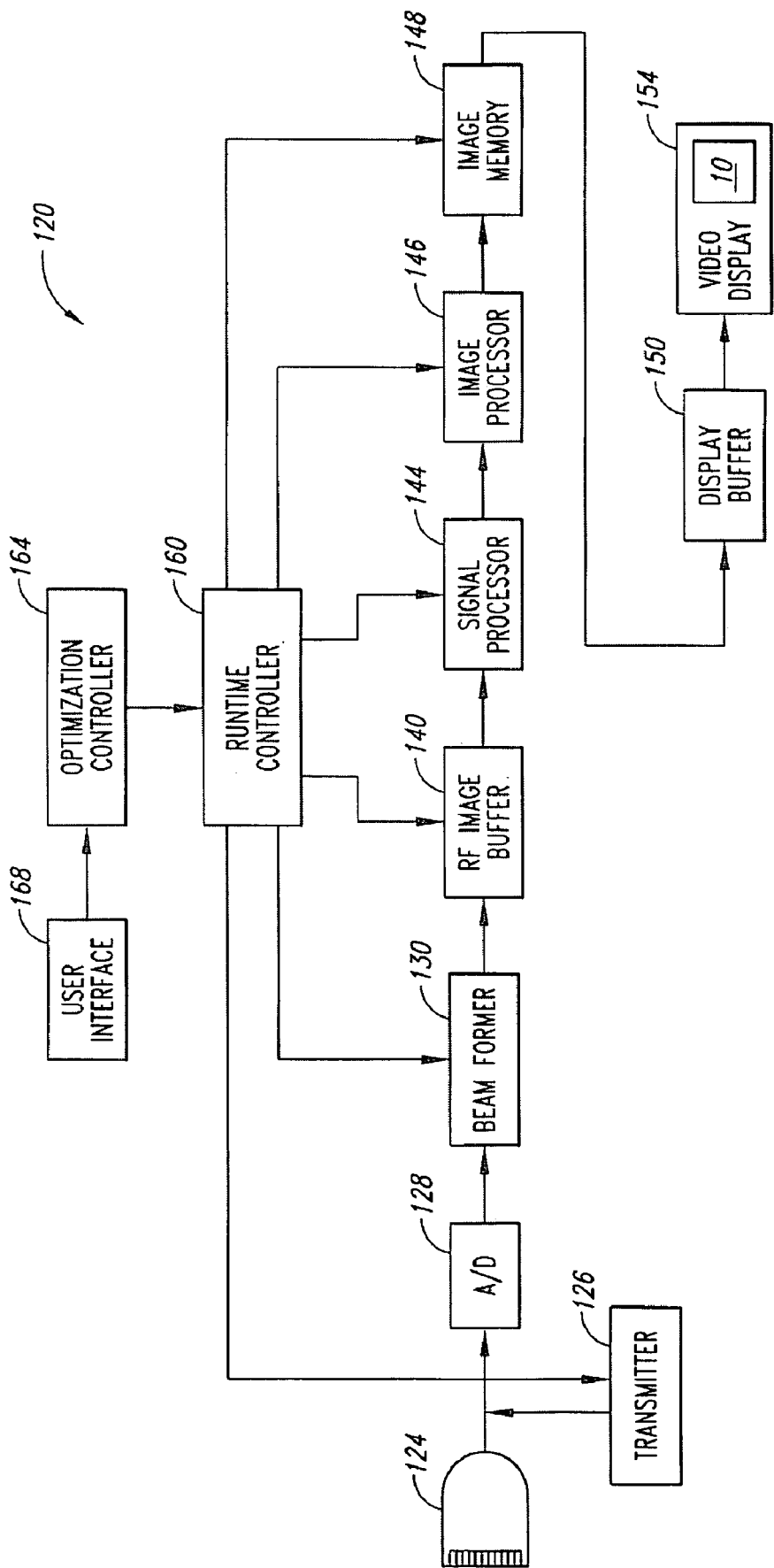
FIG. 6 is a block diagram of an ultrasound imaging system according to another embodiment of the invention.

One limitation of the imaging system 90 shown in FIG. 5 is that each of several images having different settings may have to be obtained at different times because there may be no means to obtain them from the same image data. As a result, there is a possibility that differences in the appearance between images using different settings may be caused by different image data rather than the different settings. Another embodiment of an ultrasound imaging system 120 shown in FIG. 6 avoids this limitation. The imaging system 120 includes a scanhead 124 that performs the same function as the scanhead 94 of FIG. 5, a transmitter 126 that performs the same function as the transmitter 96 of FIG. 5, an A/D converter 128 that performs the same function as the A/D converter 98 of FIG. 5, and a digital beamformer 130 that performs the same function as the digital beamformer 100. The system 120 also includes an RF image buffer 140 that receives and stores sequences of focused, coherent digital echo samples taken along each scanline. These samples can be processed to produce different images using different settings so that the same image data is used for all of these images. Any difference between the images will therefore be caused by differences in the settings. For settings which vary in transmit parameters, different images can be acquired using the different transmit parameters being offered. It may be desirable to acquire these different images so as to be visually comparable, such as by using the same triggering (gating) for each image or acquiring the images in very rapid succession or by interleaving the acquisition.

The echo samples stored in the RF image buffer 140 are applied to a signal processor 144, which performs some of the same functions performed by the signal processor 110 of FIG. 5. The signals processed by the signal processor 144 are then passed to an image processor 146 that performs scan conversion on the signals from the signal processor 144. These converted signals are then stored in an image memory 148. The image memory 148 provides much the same advantages as the RF image buffer 140. Specifically, the signals stored in the image memory 148 can be used to generate multiple images each using different display settings so that differences in the appearances of the images will be solely caused by the differences in the settings. The signal from the image memory 148 that are currently being displayed are applied to and stored in a display buffer 150. The image signals stored in the display buffer 150 are coupled to a video display 154, which includes the viewing screen 10 shown in FIGS. 1–5.

The operations of the transmitter 126 the digital beamformer 130, the RF image buffer 140, the signal processor 144, the image processor 144 and the image memory 148 are controlled by a runtime controller 160, which may be a programmed microprocessor, a logic circuit or some other type of circuit. The runtime controller 160 also interfaces with an optimization controller 164, which may also be a programmed microprocessor, a logic circuit or some other type of circuit. The optimization controller 164 is interfaced with a user interface 168 that, among other things, allows a system operator to select images displayed on the screen 10, thereby selecting corresponding settings, as previously explained.

The selection of an image or images from the gallery of images may be done by using the screen cursor and trackball conventionally provided with an ultrasound system, or by means of a touchscreen or voice recognition command.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of setting-up an ultrasound imaging system, comprising:
   using the ultrasound imaging system to display a gallery of ultrasound images each of which is obtained using a different setting for the ultrasound imaging system;
   selecting at least one of the displayed ultrasound images; and
   setting up the ultrasound imaging system using the setting for the at least one selected ultrasound image.

2. The method of claim 1 wherein the different settings comprise different image acquisition settings.

3. The method of claim 1 wherein the different settings comprise different signal processing settings.

4. The method of claim 1 wherein the different settings comprise different image processing settings.

5. The method of claim 1 wherein the different settings comprise the use of different operating modes.

6. The method of claim 5 wherein the different operating modes comprise one or more of the modes of M-mode, two-dimensional imaging, three-dimensional imaging, harmonic imaging, fundamental imaging, grayscale imaging and Doppler imaging.

7. The method of claim 1 wherein the act of using the ultrasound imaging system to display a gallery of ultrasound images comprises using the ultrasound imaging system to display a gallery of thumbnail images in a first window, and wherein the method further comprises displaying an image using the settings used to generate the selected images.

8. The method of claim 1 wherein the act of using the ultrasound imaging system to display a gallery of ultrasound images comprises displaying a gallery of ultrasound images each of which is obtained using a different setting for the same acquisition or display parameter.

9. The method of claim 1 further comprising designating the type of ultrasound examination that will be conducted, and wherein the act of using the ultrasound imaging system to display a gallery of ultrasound images comprises displaying different galleries of images obtained using different settings based on the designated type of ultrasound examination that will be conducted.

10. The method of claim 1 wherein the act of using the ultrasound imaging system to display a gallery of ultrasound images comprises displaying a gallery of ultrasound images each of which is obtained using a different combination of settings.

11. The method of claim 1 further comprising manually adjusting at least one setting after the ultrasound imaging system has been set up by selecting at least one of the ultrasound images in the gallery.

12. The method of claim 1 wherein the act of using the ultrasound imaging system to display a gallery of ultrasound images comprises displaying the gallery of ultrasound images based on the settings used to obtain an image previously selected from a displayed gallery.

13. The method of claim 1 wherein the act of using the ultrasound imaging system to display a gallery of ultrasound images comprises displaying the gallery of ultrasound images based on the type of ultrasound imaging examination that is to be performed.

14. The method of claim 1 wherein the different settings comprise one or more of the settings of line density, focal zones, dynamic range, transmit and receive frequencies, resolution, penetration, transmit power, sector width, grayscale mapping, number of multilines, wall filter settings, color map, frame rate, velocity range, frequency compounding, filter settings, filtering, persistence, and steering angle.

15. A diagnostic ultrasound imaging system, comprising:
   an ultrasound scanhead having a plurality of transducer elements;
   a transmitter coupled to the scanhead, the scanhead being operable to apply a transmit signal to the scanhead;
   a beamformer coupled to the scanhead, the beamformer being operable to receive signals corresponding to ultrasound echoes from the scanhead and generate scan line signals corresponding thereto;
   a signal processor coupled to the beamformer, the signal processor processing the scan line signals according to a setting of the imaging system;
   an image processor coupled to the signal processor, the image processor receiving signals corresponding to an image frame and generating from the signals corresponding to the composite image frame corresponding video signals;
   a video display coupled to the image processor for receiving the video signals and displaying corresponding ultrasound images;
   a user interface operable to allow images shown on the video display to be selected; and
   a controller coupled to the signal processor and the image processor, the controller controlling the operation of the signal processor and image processor in accordance with settings for the imaging system, the controller being operable to cause a gallery of ultrasound images obtained using different settings to be shown on the video display, the controller responding to at least one of the displayed ultrasound images being selected to operate at least one of the signal processor and the image processor using the setting that was used to obtain the selected ultrasound image.

16. The ultrasound imaging system of claim 15 wherein the controller is operable to allow a plurality of displayed ultrasound images to be sequentially selected and to operate at least one of the signal processor and the image processor using all of the setting that were used to obtain the selected ultrasound images.

17. The ultrasound imaging system of claim 15 wherein the controller is operable to cause a gallery of ultrasound images obtained using different combinations of settings to be shown on the video display, and wherein the controller is responsive to one of the displayed ultrasound images being selected to operate at least one of the signal processor and the image processor using the combination of settings that was used to obtain the selected ultrasound image.

18. The ultrasound imaging system of claim 17 wherein the user interface is operable to allow selection of the type of ultrasound examination being conducted, and wherein the controller is operable select the combination of settings used to obtain the images in the gallery based on the selected ultrasound examination type.

19. The ultrasound imaging system of claim 15 further comprising an RF image buffer coupled between the beamformer and the signal processor to store the scan line signals generated by the beamformer.

20. The ultrasound imaging system of claim 15 further comprising an image memory coupled between the image processor and the video display to store the video signals generated by the image processor.

21. The ultrasound imaging system of claim 15 wherein the controller comprises:
   a runtime controller operable to control the operation of the transmitter, the beamformer, the signal processor, and the image processor;
   an optimization controller coupled to the runtime controller and the user interface, the optimization controller being operable to select the settings based on the image selected with the user interface.

22. The ultrasound imaging system of claim 15 wherein the controller is operable to select the gallery of displayed ultrasound images based on the settings used to obtain an image selected from a previously displayed gallery so that the settings for the ultrasound imaging system are iteratively selected.

* * * * *